United States Patent [19]

Stone et al.

[11] Patent Number: 4,769,450
[45] Date of Patent: Sep. 6, 1988

[54] PROCESS FOR RECOVERING CEFTAZIDIME

[75] Inventors: Thomas W. Stone, Dalton-in-Furness; Colin Robinson, Allithwaite; David G. Hughes, Puckeridge, all of England

[73] Assignee: Glaxo Group Limited, London, England

[21] Appl. No.: 63,315

[22] Filed: Jun. 18, 1987

Related U.S. Application Data

[63] Continuation of Ser. No. 709,813, Mar. 8, 1985, abandoned.

[30] Foreign Application Priority Data

Mar. 9, 1984 [GB] United Kingdom ............ 8406218

[51] Int. Cl.$^4$ ................ C07D 501/46; A61K 31/545
[52] U.S. Cl. .................................................. 540/225
[58] Field of Search .......................... 540/225, 230

[56] References Cited

U.S. PATENT DOCUMENTS

| | | | |
|---|---|---|---|
| 4,258,041 | 3/1981 | O'Callaghan et al. | 540/225 |
| 4,329,453 | 5/1982 | Brodie et al. | 540/225 |
| 4,616,080 | 10/1986 | Chou et al. | 540/225 |
| 4,659,813 | 4/1987 | Browning et al. | 540/225 |

FOREIGN PATENT DOCUMENTS

| | | |
|---|---|---|
| 1472966 | 5/1977 | United Kingdom . |
| 2025398 | 1/1980 | United Kingdom . |
| 2063871B | 6/1981 | United Kingdom . |

*Primary Examiner*—Nicholas S. Rizzo
*Attorney, Agent, or Firm*—Bacon & Thomas

[57] ABSTRACT

A process for recovering ceftazidime from an aqueous solution containing it, said solution being at a pH in the range 2.0 to 5.5, which comprises contacting the said solution with a non-functional macroreticular resin suitable for adsorbing ceftazidime, eluting the ceftazidime and isolating it, if desired in the form of a salt or hydrate.

17 Claims, No Drawings

PROCESS FOR RECOVERING CEFTAZIDIME

This application is a continuation of application Ser. No. 709,813 filed Mar. 8, 1985, now abandoned.

This invention relates to improvements in or relating to the manufacture of antibiotics. More particularly it relates to an improved process for the recovery and/or purification of ceftazidime.

Ceftazidime, which has the chemical name (6R,7R)-7-[(Z)-2-(2-aminothiazol-4-yl)-2-(2-carboxyprop-2-oxyimino)-acetamido]-3-(1-pyridiniummethyl)ceph-3-em-4-carboxylate is a valuable antibiotic. It is described inter alia in United Kingdom Patent Specification No. 2025398 and details of its preparation are given therein. Salts and hydrates of ceftazidime are also described in this United Kingdom Patent. A preferred form of ceftazidime, the pentahydrate, is described in United Kingdom patent Specification No. 2063871.

The pentahydrate is obtained in highly pure form but under certain circumstances it may be necessary to recover and/or purify ceftazidime. Thus, for example, at the final preparative stage of its manufacture, ceftazidime may be obtained in an aqueous solution, which may also contain other substances such as inorganic or organic salts, high molecular weight impurities and/or degradation products. Ceftazidime may be isolated from this solution, for example, by adjusting to a pH in the range 2.7 to 4.8 and precipitating highly pure ceftazidime in the form of its pentahydrate, as described in United Kingdom Pat. No. 2063871. However, a significant amount of ceftazidime may remain in solution at low concentration, and it is desirable, especially on a manufacturing scale, to recover this dissolved ceftazidime, free from the other substances which may be present in the solution. Recovery of material from dilute solutions such as these on a manufacturing scale is difficult to effect efficiently using conventional methods for example recrystallisation, or salting-out.

In addition, it may be necessary to purify batches of ceftazidime which do not meet the required standards.

Pharmaceutical formulations of ceftazidime, which may be blended with one or more bases may also require reprocessing.

We have now found that ceftazidime may be efficiently recovered from an aqueous solution containing it and, if necessary, purified, by adsorbing the solution at a pH in the range 2.0 to 5.5 onto a non-functional macroreticular resin (also known as non-ionic macroporous resin) and subsequently eluting the ceftazidime, which is obtained in high yield and in pure form. United Kingdom Patent Specification No. 2025398 describes in Example 1(c) a method for the purification of ceftazidime during its synthesis involving the adsorption of the monosodium salt from a relatively concentrated solution at pH6 onto a non-functional macroreticular resin, followed by elution. However, recovery of sodium ceftazidime was relatively low, apparently because, as we have subsequently discovered, ceftazidime is only very weakly adsorbed onto such resins at pH6.

United Kingdom Patent Specification No. 1472966 describes a process for purifying semi-synthetic cephalosporins by adsorption onto non-functional macroreticular resins from relatively concentrated solutions under conditions at which the cephalosporin is at least 99% ionised. In the case of ceftazidime, 99% ionisation of the carboxyl function is only achieved at relatively high pH values, but we have found that at such pH levels ceftazidime is poorly adsorbed onto macroreticular resins. At very low pH, where the amino group of ceftazidime is substantially ionised, we have found that ceftazidime is also poorly adsorbed onto non-functional macroreticular resins. It is thus surprising that ceftazidime, contrary to the teaching of United Kingdom Patent Specification No. 1472966, is better adsorbed onto non-functional macroreticular resins at pH levels in the range 2.0 to 5.5 since at these pH levels ceftazidime is significantly less than 99% ionised. We have surprisingly found that ceftazidime can be very efficiently adsorbed onto non-functional macroreticular resins even from relatively dilute solutions, provided the pH of the initial solution is in the range 2.0 to 5.5, and that the ceftazidime can subsequently be eluted in very pure form. On the basis of this finding, we have found that, using the process of the invention, ceftazidime can not only be efficiently purified, for example in the context of batches not reaching the required standard, or in reprocessing mixtures containing added substances such as bases, but can also be recovered efficiently from the above mentioned relatively dilute solutions remaining after the crystallisation of ceftazidime pentahydrate.

Thus, in one aspect the invention provides a process for recovering ceftazidime from an aqueous solution containing it, said solution being at a pH in the range 2.0 to 5.5, which comprises contacting the said solution with a non-functional macroreticular resin suitable for adsorbing ceftazidime, eluting the ceftazidime and isolating it, if desired in the form of a salt or a hydrate.

Non-functional macroreticular resins which may be employed in the process of the invention typically have a surface area of from 200 to 1200 $m^2/g$, e.g. 300 to 950$m^2/g$ and an average pore diameter of from 2 to 18 nm, e.g. 3 to 15 nm. The resin may be for example a copolymer of styrene cross-linked with divinyl benzene such as Amberlite XAD-2, XAD-4 and XAD-1180 (Rohm and Haas), Diaion HP-20 and HP-21 (Mitsubishi), Duolite S861, S8602 or ES865 (Rohm & Haas) and Kastell-S111 and S112 (Montedison); or a substituted (e.g. halogenated) copolymer of styrene cross-linked with divinyl benzene, e.g. Diaion SP-207 (Mitsubishi; a brominated copolymer).

The process according to the invention is particularly suitable for recovery of ceftazidime from relatively dilute aqueous solutions, such as the mother liquors from precipitation of ceftazidime pentahydrate mentioned above. Thus, the process is of particular use where the concentration of ceftazidime is below 10% by weight, especially in the range 0.5 to 8.0% by weight. It will be appreciated that elution can be effected using relatively small volumes of eluant to effect an overall concentration, thereby facilitating a further precipitation step, which precipitation may for example be carried out as described in United Kingdom Patent Specification No. 2063871.

As indicated above, the aqueous ceftazidime solution to be treated according to the invention may contain impurities, such as high molecular weight impurities, degradation-products and/or one or more salts. The latter may be salts of inorganic or organic acids, such as halides e.g. chlorides; sulphates; nitrates; phosphates; formates and acetates. They may be salts with alkali metals such as sodium or potassium or alkaline earth metals such as calcium; ammonium salts; or salts with amino acids such as lysine or arginine. The salts present in the solution will generally be derived from the manufacturing or formulation processes. As indicated above, a base may also be present, as where certain formulations of ceftazidime are reprocessed.

The aqueous ceftazidime solution for adsorption onto the resin (i.e. the input solution) may also contain a small amount of a water-miscible organic solvent, for example less than 10% by volume, preferably less than 5%.

As indicated above, the aqueous ceftazidime solution to be contacted with the non-functional macroreticular resin will be at a pH of from 2.0 to 5.5. However, more preferably, the pH is in the range 2.7 to 4.8, advantageously 3.0 to 4.2. If necessary the pH of the solution may be adjusted before contacting it with the resin. The pH adjustment may if desired be effected by treatment with an ion exchange resin.

The aqueous solution containing ceftazidime to be recovered according to the invention may be brought into contact with the non-functional macroreticular resin in any desired way, most suitably by passing it through a column or bed of granular resin e.g. in conventional bead form. If desired the resin may be slurried with the ceftazidime solution. When a column system is used, the slurrying may be effected either prior to filling the column or in the column itself.

When the ceftazidime has been adsorbed onto the resin, the resin may, if necessary, be washed with water prior to elution, to remove salts which may be present.

Ceftazidime may be eluted from the resin using one or more water-miscible organic solvents in admixture with water. Examples of the organic component of the eluant include water-miscible ketones, such as acetone; ethers such as tetrahydrofuran, dioxan or diethyl ether; esters, such as ethyl acetate; nitriles such as acetonitrile; or alcohols such as methanol, ethanol, isopropanol or industrial methylated spirits. The organic solvent(s) generally comprise 5 to 90% of the total volume of the eluant, for example 5 to 50% preferably 10 to 30%.

The eluant may, for example, be at a pH in the range 2.0 to 10.0, conveniently at an approximately neutral pH; if desired the pH of the eluant may be adjusted in this range by addition of an acid or base, or by using a buffer, for example an acetate buffer.

The adsorption and elution of ceftazidime on the resin are conveniently effected at a temperature of from 0° to 50° C., preferably 15° to 25° C.

It will be appreciated that where impurities are present which are adsorbed by the resin the elution conditions will desirably be chosen so as to effect chromatographic separation of ceftazidime from the impurities. Thus, for example, after washing the resin with water to remove any salts present, the initial eluate fractions may be discarded until elution of ceftazidime commences. The ceftazidime containing fractions may then be collected until the ceftazidime has substantially been eluted from the resin and before adsorbed impurities are eluted. The presence of ceftazidime in the eluate may be detected by using conventional analytical techniques, such as high performance liquid chromatography (HPLC), ultra-violet spectroscopy or measurement of optical rotation. In general, the volume of eluate containing the eluted ceftazidime will be substantially less than that of the input solution, so that some overall concentration is effected.

In order to isolate ceftazidime from the eluate obtained in the process of the invention, this solution may be treated in any conventional manner. Thus, for example, ceftazidime may be crystallised directly from the eluate by seeding and/or cooling the solution. Preferably the organic solvent is removed from the eluate for example by distillation or evaporation, prior to isolating the ceftazidime. In order to facilitate crystallisation it may be desirable to concentrate the aqueous solution, e.g. by heating under vacuum, e.g. at a vapour temperature of 10°–60° C., preferably 10°–40° C. The crystallisation of ceftazidime is preferably effected at a temperature of below 35° C., advantageously below 25° C.

Ceftazidime may if desired be isolated from the eluate as a salt (e.g. the sodium salt or bishydrochloride) or a hydrate e.g. the pentahydrate. A salt of ceftazidime may be formed by adding an appropriate acid or base to the eluate and precipitating the desired salt. Alternatively, if the eluant contains an appropriate acid or base, the salt may be precipitated directly from the eluate, generally after adjustment of the pH and/or concentration of the eluate.

A particularly preferred method of obtaining crystalline ceftazidime from the eluate comprises adjusting the pH of the eluate to about pH6, followed by removal of the organic solvent, as described above, and adding an acid to the resulting aqueous solution until the pH is in the range 2.7 to 4.8, preferably 3.5 to 4.2. Ceftazidime may be crystallised from this solution in the form of its pentahydrate. Suitable acids and bases for use in this preferred method are described in United Kingdom Patent Specification No. 2063871.

The following non-limiting examples illustrate the invention.

EXAMPLES 1–35

Method

A solution containing ceftazidime together with impurities was loaded on to a glass column packed with resin. The column was washed with water and then eluted with an aqueous organic eluant. An initial eluate fraction was collected and discarded. The principal eluate fraction was collected and the pH adjusted using 2N sodium hydroxide solution (except in Example 21 where the pH was adjusted using 2N sulphuric acid). The resulting solution was concentrated in vacuo and crystallised by adding 2N sulphuric acid to pH 3.6 to 3.8 at 20° to 22° C. (except in Example 21 where crystallisation was effected by the addition of concentrated hydrochloric acid and acetone at 25° to 35° C.). After cooling to 5° C. the solid was filtered, washed with chilled water and acetone (at ambient temperature) and then dried. The product was shown to be ceftazidime by HPLC assay, and moisture content was determined by Karl Fischer analysis.

The results of these Examples are given in Table I.

Apart from Example 21, the product of each Example in Table I is ceftazidime pentahydrate.

The product of Example 21 is ceftazidime bishydrochloride.

The following abbreviations are used in Table I to designate the resins and eluants:

| Abbreviation | Resin (Specific surface area m²/g, Pore volume ml/g, Average pore radius, nm) |
| --- | --- |
| Ra | Amberlite XAD-1180 Rohm and Haas (650 m²/g, 1.7 ml/g). |
| Rb | Diaion SP207, Mitsubishi - a brominated co-polymer of styrene cross-linked with divinylbenzene, containing ca. 17% bromine (400 m²/g, 0.5 ml/g). |
| Rc | A chlorinated co-polymer of styrene cross- |

| Abbreviation | Resin (Specific surface area m²/g, Pore volume ml/g, Average pore radius, nm) |
|---|---|
| | linked with divinyl benzene, containing 17.8% chlorine, Rohm and Haas. |
| Rd | Duolite S8602, Rohm and Haas (360–440 m²/g) |
| Re | Amberlite XAD-2, Rohm and Haas (300 m²/g, 684 ml/g, 9 nm) |
| Rf | Duolite S861, Rohm and Haas (540–660 m²/g). |
| Rg | Diaion HP21, Mitsubishi, (700 m²/g, 0.85 ml/g). |
| Rh | Diaion HP20, Mitsubishi (718 m²/g, 1.16 ml/g) |
| Ri | Kastell S-111, Montedison (500–800 m²/g, 0.6–1.2 ml/g, 2–3 nm). |
| Rj | Kastell S-112 Montedison (450–600 m²/g, 1–1.8 ml/g, 4–6 nm). |
| Rk | Amberlite XAD-4, Rohm and Haas (784 m²/g, 0.976 ml/g, 4 nm). |

Physical characteristics are quoted for the dry resin.

| Abbreviation | Eluant |
|---|---|
| Ea | acetone-water |
| Eb | acetonitrile-water |
| Ec | diethyl ether-water |
| Ed | tetrahydrofuran-water |
| Ee | ethyl acetate-water |
| Ef | industrial methylated spirit-water |
| Eg | dioxan-water |
| Eh | isopropyl alcohol-water |
| Ei | methanol-water |

4,769,450

| Example number | Resin type | Input Solution | | | | Water Washing | | Eluant | | Elution | | | Adjusted pH of principal fraction | Volume after concentration (cm³) | Yield of ceftazidime (g) | % water (Karl Fischer) | HPLC Assay (% purity) |
|---|---|---|---|---|---|---|---|---|---|---|---|---|---|---|---|---|---|
| | | Volume of Resin (cm³) | Volume (cm³) | Weight of ceftazidime (g) | Rate of loading (cm³/h) | pH | Volume (cm³) | Rate (cm³/h) | Composition | % v/v organic solvent | Rate (cm³/h) | Initial fraction (cm³) | Principal fraction (cm³) | | | | | |
| 1 | Ra | 500 | 1500 | 22.5 | 1500 | 3.6 | 1000 | 1000 | Ea | 15 | 500 | 500 | 450 | 6.0 | 100 | 14.7 | 15.0 | 99.1 |
| 2 | Rb | 250 | 1350 | 22.5 | 250 | 3.6 | 250 | 250 | Ea | 20 | 250 | 235 | 485 | 6.0 | 108 | 15.84 | 14.6 | 98.6 |
| 3 | Ra | 500 | 2000 | 25.5 | 1000 | 3.8 | 500 | 1000 | Ea | 16 | 500 | 500 | 920 | 6.0 | 125 | 17.39 | 14.4 | 96.3 |
| 4 | Ra | 500 | 1530 | 23.0 | 1000 | 3.8 | 500 | 1000 | Eb | 16 | 500 | 575 | 685 | 5.5 | 109 | 16.99 | 15.0 | 98.9 |
| 5 | Ra | 500 | 1530 | 23.0 | 1000 | 3.8 | 500 | 1000 | Ec | 7.5 | 500 | 554 | 1110 | 5.3 | 116 | 13.34 | 13.8 | 97.3 |
| 6 | Ra | 500 | 1530 | 23.0 | 1000 | 3.8 | 500 | 1000 | Ed | 16 | 500 | 530 | 640 | 5.3 | 112 | 14.27 | 14.8 | 98.1 |
| 7 | Ra | 500 | 1700 | 25.5 | 1000 | 3.8 | 500 | 1000 | Ee | 7.9 | 500 | 445 | 915 | 5.8 | 129 | 18.17 | 14.6 | 97.9 |
| 8 | Ra | 500 | 1700 | 25.5 | 1000 | 3.8 | 500 | 1000 | Ef | 16 | 500 | 440 | 1245 | 5.5 | 101 | 16.63 | 14.4 | 97.3 |
| 9 | Ra | 500 | 1530 | 23 | 1000 | 3.8 | 500 | 1000 | Eg | 16 | 500 | 482 | 670 | 5.5 | 115 | 14.66 | 15.0 | 98.6 |
| 10 | Ra | 500 | 1700 | 25.5 | 1000 | 3.8 | 500 | 1000 | Ei | 16 | 500 | 600 | 1500 | 6.0 | 115 | 9.92 | 14.0 | 94.8 |
| 11 | Ra | 500 | 1254 | 23.2 | 1000 | 3.8 | 500 | 1000 | Eh | 16 | 500 | 500 | 760 | 6.0 | 113 | 16.79 | 13.8 | 96.6 |
| 12 | Rc | 440 | 1349 | 20.24 | 880 | 3.7 | 440 | 880 | Ea | 14 | 440 | 430 | 735 | 5.6 | 88 | 10.76 | 13.9 | 97.7 |
| 13 | Rd | 320 | 981 | 14.72 | 640 | 3.65 | 320 | 640 | Ea | 16 | 320 | 290 | 580 | 5.5 | 72 | 11.44 | 14.9 | 98.1 |
| 14 | Re | 470 | 1441 | 21.62 | 940 | 3.7 | 470 | 940 | Ea | 16 | 470 | 405 | 600 | 5.6 | 64 | 7.0 | 14.8 | 97.4 |
| 15 | Rf | 500 | 1533 | 23.0 | 1000 | 3.7 | 500 | 1000 | Ea | 16 | 500 | 520 | 755 | 5.6 | 110 | 17.48 | 14.9 | 98.8 |
| 16 | Rg | 500 | 1704 | 25.53 | 1000 | 3.7 | 500 | 1000 | Ea | 16 | 500 | 410 | 860 | 5.6 | 129 | 18.54 | 14.7 | 98.4 |
| 17 | Rh | 500 | 1704 | 25.53 | 1000 | 3.7 | 500 | 1000 | Ea | 16 | 500 | 425 | 730 | 5.6 | 101 | 14.0 | 14.7 | 97.4 |
| 18 | Ri | 250 | 765 | 11.5 | 500 | 4.1 | 250 | 500 | Ea | 16 | 250 | 246 | 580 | 5.5 | 47 | 7.0 | 13.9 | 96.4 |
| 19 | Rj | 500 | 1278 | 23.0 | 1000 | 3.7 | 500 | 1000 | Ea | 16 | 500 | 500 | 1010 | 5.4 | 98 | 16.7 | 15.3 | 98.7 |
| 20 | Rk | 500 | 1278 | 23.0 | 1000 | 3.7 | 500 | 1000 | Ea | 16 | 500 | 455 | 1210 | 5.5 | 82 | 9.4 | 15.3 | 98.2 |
| 21 | Ra | 500 | 1971 | 23.0 | 1000 | 3.65 | 500 | 1000 | Ea | 16 | 500 | 450 | 752 | 2.9 | 79 | 17.90 | — | 92.9 |
| 22 | Ra | 500 | 1500 | 22.5 | 1000 | 3.8 | 750 | 1000 | Ea | 10 | 500 | 580 | 550 | 3.8 | 105 | 12.79 | 13.4 | 96.0 |
| 23 | Ra | 500 | 1216 | 22.5 | 1000 | 3.8 | 750 | 1000 | Ea | 15 | 1000 | 550 | 580 | 6.0 | 100 | 14.81 | — | — |
| 24 | Ra | 500 | 1500 | 22.5 | 1000 | 3.8 | 1000 | 1000 | Ea | 20 | 500 | 480 | 420 | 6.0 | 100 | 13.94 | — | — |
| 25 | Ra | 500 | 1500 | 23.0 | 1000 | 3.8 | 500 | 1000 | Ea | 25 | 500 | 620 | 600 | 6.0 | 148 | 13.83 | 14.9 | 97.8 |
| 26 | Ra | 500 | 1500 | 23.0 | 1000 | 3.8 | 500 | 1000 | Ea | 30 | 500 | 140 | 860 | 6.0 | 150 | 14.9 | 14.7 | 97.5 |
| 27 | Ra | 500 | 1300 | 23.0 | 1000 | 2.0 | 500 | 1000 | Ea | 16 | 500 | 500 | 800 | 6.0 | 120 | 9.75 | 15.7 | 99.6 |
| 28 | Ra | 500 | 833 | 23.0 | 1000 | 3.0 | 500 | 1000 | Ea | 16 | 500 | 520 | 710 | 6.0 | 99 | 15.83 | — | — |
| 29 | Ra | 500 | 1438 | 23.0 | 1000 | 3.7 | 500 | 1000 | Ea | 16 | 500 | 565 | 810 | 6.0 | 125 | 17.85 | — | — |
| 30 | Ra | 500 | 1916 | 23.0 | 1000 | 3.9 | 500 | 1000 | Ea | 16 | 500 | 539 | 710 | 6.0 | 120 | 17.07 | — | — |
| 31 | Ra | 500 | 1916 | 23.0 | 1000 | 4.3 | 500 | 1000 | Ea | 16 | 500 | 529 | 650 | 6.0 | 110 | 10.96 | 14.6 | 97.7 |
| 32 | Ra | 500 | 1840 | 23.0 | 1000 | 5.0 | 500 | 1000 | Ea | 16 | 500 | 500 | 500 | 6.0 | 75 | 2.05 | — | — |
| 33 | Ra | 500 | 2010 | 19.89 | 1000 | 3.8 | 500 | 1000 | Ea | 16 | 500 | — | 1435 | 5.5 | 128 | 15.02 | 14.6 | 96.3 |
| 34 | Ra | 500 | 1287 | 23.2 | 1000 | 3.7 | 500 | 1000 | Ea | 16 | 500 | 200 | 1215 | 5.5 | 108 | 16.56 | 15.4 | 98.6 |
| 35 | Ra | 500 | 1250 | 25.00 | 1000 | 3.0 | 500 | 1000 | Ea | 16 | 500 | 500 | 775 | 5.5 | 115 | 17.76 | 14.3 | 99.2 |
| 36 | Ra | 500 | 2120 | 22.26 | 1000 | 3.7 | 500 | 1000 | Ea | 16 | 500 | 480 | 707 | 6.1 | 115 | 17.56 | 14.7 | 98.7 |

Footnotes to Table I
(1) The weight of ceftazidime in the input solution (by HPLC assay) is given as the weight of ceftazidime pentahydrate.
(2) The purity by HPLC is corrected for water content.

Preparation of starting solutions

The input solutions used in Examples 1-35 were derived as follows:

Input for Examples 1-32

Ceftazidime bishydrochloride (95.3% pure) was dissolved in water and the pH adjusted to 6.0 by the addition of 2N sodium hydroxide. Ceftazidime pentahydrate was crystallised from this solution by adjustment to a pH in the range 3.0 to 4.0, using 2N sulphuric acid.

The crystalline ceftazidime pentahydrate was filtered and the solid washed with water followed by acetone. The combined filtrate and aqueous washings formed the input solution.

Input to Example 33

A mixture of ceftazidime pentahydrate (200 g) and sodium carbonate (20 g) was dissolved in water. Ceftazidime pentahydrate was crystallised by adjusting the solution to a pH in the range 3.0 to 4.0 using 2N sulphuric acid.

The crystalline ceftazidime pentahydrate was removed by filtration and washed with water, followed by acetone. The combined filtrate and aqueous washings formed the input solution.

Input to Example 34

A mixture of ceftazidime pentahydrate (200 g) and L-arginine (59.1 g) was dissolved in water. Ceftazidime pentahydrate was crystallised as in Example 33 and the combined filtrate and aqueous washings formed the input solution.

Input to Example 35

Ceftazidime pentahydrate (25 g, ca 96.1% pure) was dissolved in water, by addition of sodium carbonate (2.5 g) to pH 6. The solution was then adjusted to pH 3 with 2N sulphuric acid, to form the input solution.

EXAMPLE 36

(a) Ceftazidime bishydrochloride (200 g, ca 96.0% pure by HPLC and having an unacceptable level of coloured impurities) was dissolved in water and the pH of the solution was adjusted to 6.0 using 2N sodium hydroxide. Ceftazidime pentahydrate was precipitated by adding 2N sulphuric acid until the pH of the solution was in the range 3.0 to 4.0. The crystalline ceftazidime pentahydrate was filtered and washed with water. The combined filtrate and washings formed the input solution to Part (b).

(b) The aqueous solution containing ceftazidime obtained in Part (a) was treated according to the general method given above for Examples 1-35. Experimental details and results are given in Table I. The product (ceftazidime pentahydrate) showed a 3-fold reduction in the level of coloured impurities as compared with the starting material for Part (a), and was of acceptable quality.

EXAMPLE 37

(a) Ceftazidime pentahydrate (200 g, ca 96.1% pure) was dissolved in water by addition of 2N sodium hydroxide to pH 6. The pentahydrate was recrystallised by adjusting the pH of the solution from 3.6 to 3.8 at 20° to 22° C. The crystalline solid was filtered and washed with water, to give the first crop of ceftazidime pentahydrate (155.9 g, moisture content (Karl Fischer) 13.7%, HPLC assay (corrected for moisture) 96.6%). The combined filtrate and washings formed the input solution to Part (b).

(b) The aqueous solution containing ceftazidime (34.96 g) obtained in Part (a), was loaded at pH 3.6 on to a glass column packed with Rohm and Haas resin XAD-1180 (800 cm$^3$) at a rate of 800 cm$^3$/h. The column was washed with water (800 cm$^3$) at 400 cm$^3$/h and then eluted with 16% v/v acetone/water at 400 cm$^3$/h. An initial eluate fraction (810 cm$^3$) was collected and discarded. The principal eluate fraction (910 cm$^3$) was collected and adjusted to pH 5.5 using 2N sodium hydroxide solution. This solution was then concentrated to a volume of 175 cm$^3$ and crystallised by the addition of 2N sulphuric acid to pH 3.6 at 20° to 22° C. After cooling to 5° C. the solid was filtered, washed with chilled water followed by acetone and then dried, to give ceftazidime pentahydrate (27.42 g).

Moisture content (Karl Fischer) 13.6%

HPLC essay (corrected for moisture content) 97.7%.

(c) The product obtained in Part (a) was combined with the product obtained in Part (b), and a portion of this material (20 g) was dissolved in water by adjustment to pH 6 using 2N sodium hydroxide solution. Addition of 2N sulphuric acid to pH 3.6-3.8 at 20° to 22° C. gave a crystalline precipitate. After cooling to 5° C. the solid was filtered, washed with chilled water followed by acetone, and then dried to give ceftazidime pentahydrate (17.53 g).

Moisture content (Karl Fischer) 14.3%

HPLC assay (corrected for moisture content) 98.1%.

EXAMPLES 38-41

Method

A solution containing ceftazidime (23 g) together with impurities at pH 3.8 was loaded on to a glass column packed with Rohm and Haas resin Amberlite XAD-1180 (500 cm$^3$) at a rate of 1000 cm$^3$/hour and at a specified temperature. The column was washed with water (500 cm$^3$) at a rate of 1000 cm$^3$/hour, and then eluted with 16% v/v acetone/water at 500 cm$^3$/hour, also at a specified temperature. An initial eluate fraction was collected and discarded. The principal eluate fraction was collected and adjusted to pH 6.0, using 2N sodium hydroxide solution. This solution was then concentrated in vacuo and crystallised to give ceftazidime pentahydrate by adding 2N sulphuric acid to pH 3.6-3.8 at 20°-22° C. After cooling to 5° C. the solid ws filtered, washed with chilled water followed by acetone and then dried. The product was shown to be ceftazidime by HPLC assay, and moisture content was determined by Karl Fischer analysis.

The results are given in Table II.

The starting solutions for Examples 38-41 were prepared as for Examples 1-32.

| Example number | Volume of input (cm$^3$) solution | Temperature of loading (°C.) | Temperature of Elution (°C.) | Initial fraction (cm$^3$) | Principal fraction (cm$^3$) | Volume after concentration (cm$^3$) | Yield of ceftazidime (g) | Water (Karl Fischer) % | HPLC Assay (% purity) |
|---|---|---|---|---|---|---|---|---|---|
| 38 | 1500 | 25 | 25 | 340 | 1050 | 120 | 14.94 | 15.1 | 99.8 |
| 39 | 1620 | 25 | 5 | 490 | 1650 | 120 | 14.51 | 15.4 | 98.4 |
| 40 | 1620 | 5 | 25 | 150 | 725 | 110 | 14.26 | 15.6 | 98.6 |

-continued

| Example number | Volume of input (cm³) solution | Temperature of loading (°C.) | Temperature of Elution (°C.) | Initial fraction (cm³) | Principal fraction (cm³) | Volume after concentration (cm³) | Yield of ceftazidime (g) | Water (Karl Fischer) % | HPLC Assay (% purity) |
|---|---|---|---|---|---|---|---|---|---|
| 41 | 1500 | 5 | 5 | 450 | 1250 | 125 | 13.33 | 15.3 | 95.0 |

We claim:

1. A process for recovering ceftazidime, a salt or hydrate thereof, from an aqueous solution containing ceftazidime, said solution being at a pH in the range 2.0 to 5.5 which comprises contacting said solution with a non-functional macroreticular resin suitable for adsorbing ceftazidime, eluting and isolating ceftazidime or a salt or hydrate thereof.

2. A process as claimed in claim 1 in which the non-functional macroreticular resin is a co-polymer of styrene cross-linked with divinyl benzene, which polymer may be substituted.

3. A process as claimed in claim 2 in which the resin has a surface area of from 200 to 1200 m²/g and an average pore diameter from 2 to 18 nm.

4. A process as claimed in claim 1 in which the pH of said aqueous solution is in the range 2.7 to 4.8.

5. A process as claimed in claim 4 in which said pH is in the range 3.0 to 4.2.

6. A process as claimed in claim 1 in which elution is effected using one or more water-miscible organic solvents in admixture with water.

7. A process as claimed in claim 6 in which the organic solvent is selected from the group consisting of water-miscible ketones; ethers; esters; nitriles; alcohols and mixtures thereof.

8. A process as claimed in claim 6 in which the organic solvent comprise 5 to 50% of the total volume of eluant.

9. A process as claimed in claim 1 in which the concentration of ceftazidime in said aqueous solution contacted with a macroreticular resin is below 10 % by weight.

10. A process as claimed in claim 1 in which ceftazidime is isolated from the eluate as ceftazidime pentahydrate.

11. A process as claimed in claim 1 in which the initial aqueous solution containing ceftazidime is mother liquor remaining after precipitation of ceftazidime pentahydrate from an aqueous solution containing ceftazidime and removal of said pentahydrate.

12. In a manufacturing scale process for the production of ceftazidime, a salt or hydrate thereof, which includes precipitation of ceftazidime, a salt or hydrate thereof from an aqueous solution containing ceftazidime and which leaves an aqueous mother liquor containing unprecipitated ceftazidime, wherein the improvement comprises recovering ceftazidime, a salt or hydrate thereof from the aqueous mother liquid at a pH in the range of 2.0 to 5.5 by contacting the aqueous mother liquor having a pH or 2.0 to 5.5 with a non-functional macroreticular resin suitable for adsorbing ceftazidime, eluting and isolating ceftazidime or a salt or hydrate thereof.

13. A process as claimed in claim 12 in which the non-functional macroreticular resin is a copolymer of styrene cross-linked with divinylbenzene, which polymer may be substituted.

14. A process as claimed in claim 13 in which the resin has a surface area of from 200 to 1200 m²/g and an average pore diameter from 2 to 18 nm.

15. A process as claimed in claim 12 in which said pH is in the range 2.7 to 4.8.

16. A process as claimed in claim 15 in which said pH is in the range of 3.0 to 4.2.

17. A process as claimed in claim 12, wherein the mother liquor contains high molecular weight impurities.

* * * * *